(12) United States Patent
Johnson

(10) Patent No.: US 6,191,410 B1
(45) Date of Patent: Feb. 20, 2001

(54) FINGERPRINT SENSING APPARATUS AND METHOD

(75) Inventor: Neldon P. Johnson, American Fork, UT (US)

(73) Assignee: International Automated Systems, Inc, American Fork, UT (US)

( * ) Notice: Under 35 U.S.C. 154(b), the term of this patent shall be extended for 0 days.

(21) Appl. No.: 09/339,464

(22) Filed: Jun. 23, 1999

(51) Int. Cl.$^7$ .................................................. G01B 11/124
(52) U.S. Cl. ...................... 250/208.1; 250/216; 250/556; 382/124; 382/127
(58) Field of Search ................................. 250/208.1, 216, 250/556, 227.28, 227.29, 227.3, 227.31, 227.32; 283/68, 69, 70, 78; 356/71; 382/124, 125, 126, 127

(56) References Cited

U.S. PATENT DOCUMENTS

| | | | |
|---|---|---|---|
| 4,120,585 | 10/1978 | DePalma et al. | 356/71 |
| 4,208,651 | 6/1980 | Mcmahon | 340/146.3 E |
| 4,336,998 | 6/1982 | Ruell | 356/71 |
| 4,358,677 | 11/1982 | Ruell et al. | 250/216 |
| 4,695,716 | 9/1987 | Tandon et al. | 250/211 R |
| 5,548,394 | 8/1996 | Giles et al. | 356/71 |
| 5,598,474 | 1/1997 | Johsnon | 380/23 |
| 5,650,842 | 7/1997 | Maase et al. | 356/71 |
| 5,732,148 | 3/1998 | Keagy et al. | 382/124 |
| 5,761,330 | 6/1998 | Stoianov et al. | 382/127 |
| 5,781,651 | 7/1998 | Hsiao et al. | 382/127 |
| 5,815,598 | 9/1998 | Hara et al. | 382/211 |
| 5,822,445 | 10/1998 | Wong | 382/127 |
| 5,854,780 | * 12/1998 | Opheij et al. | 369/112 |
| 5,859,420 | 1/1999 | Borza | 250/208.1 |
| 5,886,370 | 3/1999 | Sun et al. | 257/94 |
| 5,991,431 | * 11/1999 | Borza et al. | 382/127 |

* cited by examiner

*Primary Examiner*—John R. Lee
(74) *Attorney, Agent, or Firm*—J. David Nelson

(57) ABSTRACT

A device for sensing and digitizing a fingerprint from a subject finger comprising a prism, a pixilated illuminating radiation source such as a surface-emitting laser or a radiation source and a LCD affixed to the bottom surface of the prism and providing for the internal illumination, with a plurality of sub-beams, of the contact surface where the finger of the subject is pressed and the top surface of the prism, and a photoelectric sensor to detect the sub-beam radiation reflected from the fingerprint valley points. The fingerprint ridge contact points do not reflect incident sub-beam radiation. A computer can provide for sequential emission of the sub-beams so that a single cell photoelectric sensor can be used to detect the reflected sub-beams or a multiple cell photoelectric sensor can be used, with each cell corresponding to a particular sub-beam. Reflected sub-beam radiation corresponds to a fingerprint valley point. Non-reflected sub-beam radiation corresponds to a fingerprint ridge point. The fingerprint is converted to a set of binary codes that can be used for imaging or identification purposes.

84 Claims, 2 Drawing Sheets

FINGERPRINT SENSING APPARATUS AND METHOD

FIELD OF THE INVENTION

This invention is in the field of three dimensional object sensing apparatuses and methods and more particularly in the field of apparatuses and methods for sensing fingerprints.

BACKGROUND OF THE INVENTION

Fingerprint sensing devices typically consist of a glass plate or prism upon which the finger of the subject is pressed, an illuminating light source which directs the light through the prism to the contact zone between the finger and the glass plate or prism, an image producing lens and an image capturing device such as a charge couple device (CCD). Most of these known devices function on the basic principle that if the angle of incidence of the illuminating light with the contact zone between the finger of the subject and the glass plate or prism, is adjusted to within a certain range which is dependent on the frequency of the light used, the illuminating light will be internally reflected from the contact zone at fingerprint valley points where there is no contact between the finger and the glass surface, and will not be internally reflected from the ridge points where the finger contacts the glass surface. The reflected light is focused into an image by an image producing lens and the image is transformed into an electrical signal by a CCD or other sensing device.

These known devices have inherent problems and limitations relating to the accuracy of the valley and ridge information defining the subject fingerprint. Known methods require the use of an image producing lens and require an optical sensor such as a CCD to receive the image and convert it to an electrical signal. Improvements are needed in the means and method of illuminating the contact zone between the finger and glass surface, the physical geometry of the sensing unit and the means and method of receiving and digitizing the fingerprint information.

An object of the present invention is to provide a simpler, more accurate and more reliable method and apparatus for extracting and digitizing a fingerprint for imaging and identification purposes. It is a further object of the present invention to provide a method and apparatus for utilizing a surface-emitting laser as the source of illuminating radiation. It is a further object of the present invention to provide a method and apparatus for utilizing a Liquid Crystal Display (LCD) for emitting point source radiation as the source of illuminating radiation. It is a further object of the present invention to provide a fingerprint sensing device that is durable, inexpensive and simpler to manufacture and maintain. It is a further objective of the present invention to provide an apparatus and method for the direct digitization of a fingerprint without the use of an image producing lens and optical image sensor.

SUMMARY OF THE INVENTION

Preferred embodiments of the apparatus of the present invention comprises a prism, a pixilated source of radiation, and a photoelectric sensor. For certain preferred embodiments, the prism is wedge-shaped, but it can be of any shape that provides for differentiation between fingerprint ridges and valleys. The finger of the subject is pressed to the prism top surface. For preferred embodiments, either a radiation source and a LCD or a surface-emitting laser having a network of laser vertical surface cavities, lines the prism bottom surface and the photoelectric sensor lines the prism end surface.

For embodiments using the surface emitting laser, the vertical surface cavities of the surface emitting laser are arranged in a grid network with the spacing between the cavities being selected to provide for the desired accuracy of the fingerprint extraction and digitization. Each of the surface cavities emits a laser sub-beam into the prism bottom surface when activated and each of these sub-beams is orthogonal to the top surface of the surface emitting laser and the prism bottom surface. The wedge angle between the prism top surface and the prism bottom surface determines the angle of incidence for each of the laser sub-beams. The angle of incidence of the sub-beams is selected so that the points where the fingerprint ridges of the subject contact the prism top surface will not internally reflect the laser radiation, and the points corresponding to the fingerprint valleys of the subject where the finger of the subject does not contact the prism top surface will reflect the laser radiation.

Each of the laser sub-beams illuminates a unique point on the prism top surface. Similarly, except for those points in the contact zone where the fingerprint ridges of the subject contact the prism top surface, each laser sub-beam is reflected to a unique point on the photoelectric sensor. The number of pixels and thus the accuracy of the resolution of the fingerprint extraction, is determined by the density of the surface cavities of the surface-emitting laser.

The sub-beams may be emitted sequentially in a burst and therefore sensed sequentially by a single-receptor photoelectric sensor. The photoelectric sensor may have a filter or may be tuned to detect only the frequency of radiation emitted by the laser so as to prevent interference from radiation from other sources. Alternatively, filters or shields may be installed on all exposed exterior surfaces of the prism to prevent admission of radiation to the prism from any source other than the surface emitting laser.

Each sub-beam received in its assigned time slot indicates a fingerprint valley at its corresponding point of illumination and each sub-beam not received in its assigned time slot indicates a fingerprint ridge at its corresponding point of illumination. Alternatively the photoelectric sensor may have a grid of receptors, each receptor sensing the reception of a sub-beam. The reception or non-reception of a sub-beam again indicates a fingerprint valley or ridge at the corresponding point of illumination. Either version provides for a very accurate digitization of the fingerprint, which can then be used for imaging or identification purposes. This provides for the direct digitization of the subject fingerprint without the need for an image producing lens or an optical image sensing device.

For either of the foregoing embodiments, the fingerprint apparatus of the present invention may be connected to an external computer to process the data, or may be equipped with its own computer circuit, particularly for remote applications.

For embodiments utilizing a radiation source and a LCD, the present invention functions in a manner very similar to that described above for the embodiments utilizing a surface emitting laser. Each pixel of the LCD is activated in a desired sequence thereby transmitting the light into the bottom surface of the prism and illuminating a corresponding point on the top contact surface of the prism. However, unlike the embodiments utilizing the surface emitting laser, the illuminating radiation is not confined to the corresponding point of illumination. Accordingly, the photoelectric sensor will receive reflected radiation for each pixel. If the pixel corresponds to a fingerprint ridge point, the amount of illuminating radiation reflected to the photoelectric cell will be measurably less than that reflected if the pixel corresponds to a fingerprint valley point. The difference can be increased by incorporating a minute lens at each pixel point, which lenses are affixed to the LCD or the prism or are interposed between the LCD and the prism as a lens wafer. These lenses provide for the focusing of the radiation transmitted through each pixel of the LCD on the corresponding point of illumination on the top contact surface of the prism. For these embodiments, the non-reflection of the illuminating radiation will be near total from fingerprint ridge points and the reflection of the illuminating radiation will be near total for the fingerprint valley points. This enhances differentiation between ridge points and valley points.

BRIEF DESCRIPTION OF THE DRAWINGS

The following drawings illustrate preferred embodiments of the apparatus of the present invention.

DETAILED DESCRIPTION OF PREFERRED EMBODIMENTS

Figure 1:
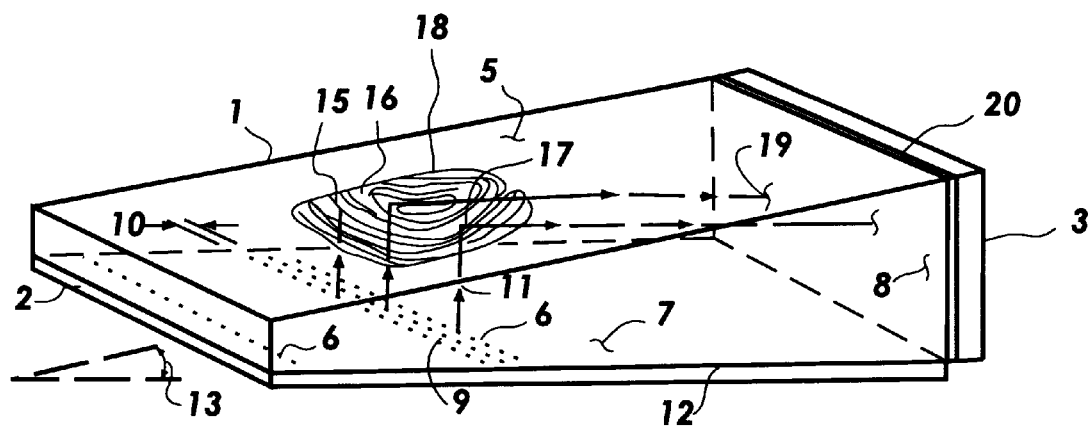
FIG. 1 is a side perspective view of a preferred embodiment of the apparatus of the present invention utilizing a surface emitting laser.
Figure 2:
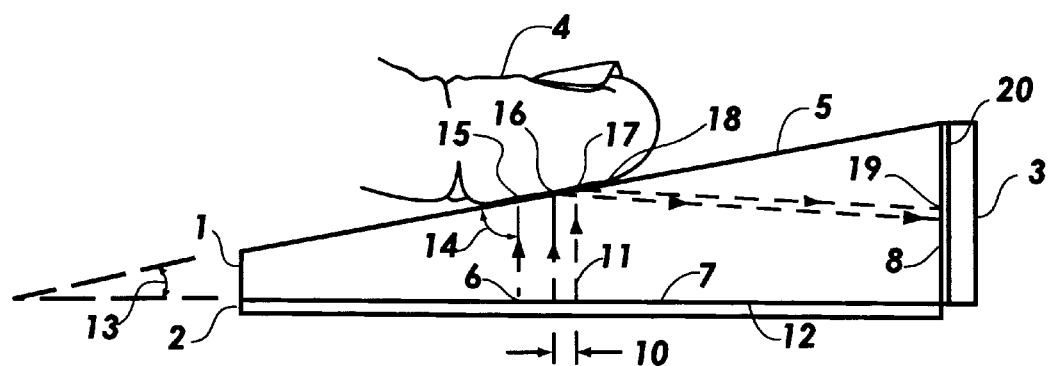
FIG. 2 is a side view of a preferred embodiment of the apparatus of the present invention utilizing a surface emitting laser.

Embodiments of the present invention utilize one of several pixilated means for internally illuminating points of illumination on a contact surface of a prism. Referring first to FIG. 1, a preferred embodiment of the apparatus of the present invention which comprises a wedge-shaped prism 1, a surface-emitting laser 2 and a photoelectric sensor 3, is illustrated therein. Referring also to FIG. 2, a finger 4 of the subject is pressed to the prism top surface 5, the contact surface, contacting the prism top surface in a contact zone 18. The surface-emitting laser, having a network of laser vertical surface cavities 6, is affixed to the prism bottom surface 7 and the photoelectric sensor is affixed to the prism end surface 8. The vertical surface cavities of the surface emitting laser are arranged in a grid network 9 with the spacing 10 between the cavities being selected to provide for the desired accuracy of the fingerprint extraction and digitization. Each of the surface cavities emits a laser sub-beam 11 into the prism bottom surface when activated and each of these sub-beams is orthogonal to the top surface 12 of the surface emitting laser and the prism bottom surface. The wedge angle 13 between the prism top surface and the prism bottom surface determines the angle of incidence 14 for each of the laser sub-beams. The angle of incidence of the sub-beams is selected so that the points where the fingerprint ridges 15 of the subject contact the prism top surface will not internally reflect the laser radiation, and the points corresponding to the fingerprint valleys 16 of the subject where the finger of the subject does not contact the prism top surface will reflect the laser radiation.

While certain preferred embodiments utilize a wedge shaped prism as illustrated in FIGS. 1 and 2, other embodiments may utilize prisms with a different shape or may utilize any medium which allows for the internal reflection of illuminating radiation at an angle which will provide for differentiation of the fingerprint ridges and valleys.

Each of the laser sub-beams illuminates a unique illumination point 17 on the prism top surface. Similarly, except for those points in the contact zone 18 where the fingerprint ridges of the subject contact the prism top surface, each laser sub-beam is reflected to a unique sensing point 19 on the photoelectric sensor. The number of pixels and thus the accuracy of the resolution of the fingerprint extraction, is determined by the density of the surface cavities of the surface-emitting laser.

The sub-beams may be emitted sequentially in a burst and therefore sensed sequentially by a single-receptor photoelectric sensor. The photoelectric sensor may have a filter 20 or may be tuned to detect only the frequency of radiation emitted by the laser so as to prevent interference from radiation from other sources. Alternatively, filters or shields may be installed on all exposed exterior surfaces of the prism to prevent admission of radiation to the prism from any source other than the surface emitting laser. Each sub-beam received in its assigned time slot indicates a fingerprint valley at its corresponding point of illumination and each sub-beam not received in its assigned time slot indicates a fingerprint ridge at its corresponding point of illumination.

Alternatively the photoelectric sensor may have a grid of receptors or sensors, each receptor or sensor sensing the reception of a unique sub-beam. For these embodiments, the sub-beams can be emitted simultaneously. The reception or non-reception of a sub-beam again indicates a fingerprint valley or ridge at the corresponding point of illumination.

The photoelectric sensor generates electric signals based upon the sub-beams received. Either of the preferred embodiments of the apparatus of the present invention described above provides for a very accurate digitization of the fingerprint, which can then be used for imaging or identification purposes. Each of these embodiments provides for the direct digitization of the subject fingerprint without the need for an image producing lens or an optical image sensing device.

Figure 3:
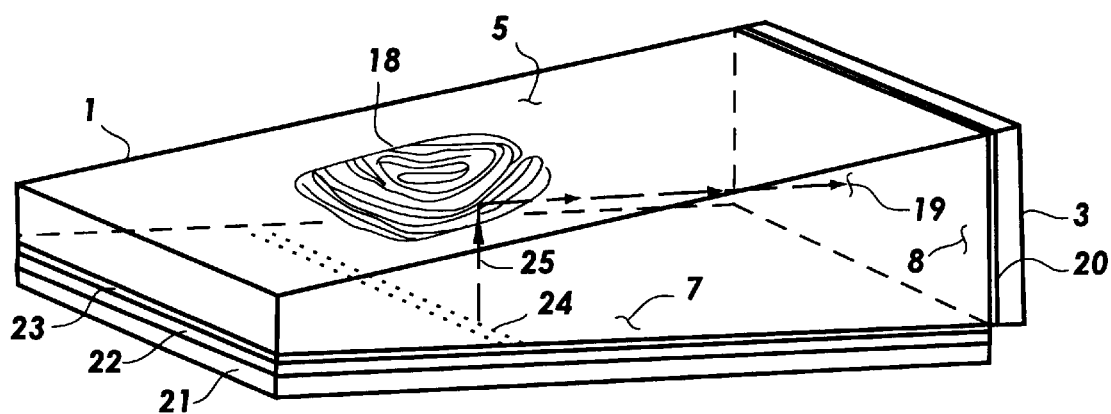
FIG. 3 is a side perspective view of a preferred embodiment of the apparatus of the present invention utilizing a radiation source and a LCD.

Referring now to FIG. 3, a preferred embodiment utilizing a radiation source 21 and a pixilated LCD 22 is illustrated. This embodiment functions in a manner very similar to that described above for the embodiments utilizing a surface emitting laser. Each pixel of the LCD is activated in a desired sequence thereby transmitting the illuminating radiation into the bottom surface of the prism and illuminating a corresponding point on the top contact surface of the prism. However, unlike the embodiments utilizing the surface emitting laser, the LCD sub-beam 25 illuminating radiation may not be confined to the corresponding discrete point of illumination. Accordingly, the photoelectric sensor will receive reflected radiation for each LCD pixel 24. If the pixel corresponds to a fingerprint ridge point, the amount of illuminating radiation reflected to the photoelectric cell will be measurably less than that reflected if the pixel corresponds to a fingerprint valley point. The difference can be increased by incorporating a minute lens at each pixel point. These lenses can be affixed to the LCD or the prism or can be interposed between the LCD and the prism as a lens wafer 23 as shown in FIG. 3. These lenses provide for the focusing of the radiation transmitted through each pixel of the LCD on the corresponding point of illumination on the top contact surface of the prism. The focal length of the lenses varies based upon the pixel location, to provide for focusing on the point of illumination. For these embodiments, the percentage of non-reflection of the illuminating radiation will be high from fingerprint ridge points and the percentage of reflection of the illuminating radiation will be high for the fingerprint valley points. This enhances differentiation between ridge points and valley points.

Any of the preferred embodiments of the fingerprint sensing apparatus of the present invention may be connected to an external computer to control the emission of the laser sub-beams and to process the electric signals generated by the photoelectric sensor or sensors, or may be equipped with its own computer circuit, particularly for remote applications where a support computer with required software is not available.

Other embodiments of the invention and other variations and modifications of the embodiments described above will be obvious to a person skilled in the art. Therefore, the foregoing is intended to be merely illustrative of the invention and the invention is limited only by the following claims.

I claim:

1. Apparatus for sensing fingerprints comprising:
   a) fingerprint differentiation means for internally reflecting illuminating radiation from points of illumination on a contact surface of the fingerprint differentiation means corresponding to fingerprint valleys in one or more fingers of the subject pressed in a contact zone on the contact surface, and for transmitting illuminating radiation through the contact surface at points of illumination corresponding to fingerprint ridges in the fingers of the subject;
   b) illuminating means affixed to the fingerprint differentiation means for internally illuminating the contact surface with a plurality of sub-beams of illuminating radiation, the angle of incidence of the sub-beams to the contact surface being selected to provide for reflection of the sub-beams from points of illumination corresponding to fingerprint valley points and transmission of sub-beams through the contact surface at fingerprint ridge points which contact the contact surface;
   c) sensing means affixed to the fingerprint differentiation means for sensing sub-beams reflected from the contact surface and generating an electric signal for each sub-beam received.

2. Apparatus as recited in claim 1 wherein the fingerprint differentiation means comprises a prism.

3. Apparatus as recited in claim 2 wherein the prism is wedge-shaped.

4. Apparatus as recited in claim 1 wherein the illuminating means comprises a surface-emitting laser.

5. Apparatus as recited in claim 1 wherein the illuminating means comprises a radiation source and a pixilated LCD.

6. Apparatus as recited in claim 5 wherein the illuminating means further comprises a focusing means for focusing the sub-beams on points of illumination on the contact surface.

7. Apparatus as recited in claim 6 wherein the focusing means comprises a lens wafer.

8. Apparatus as recited in claim 1 wherein the sensing means comprises a photoelectric sensor.

9. Apparatus as recited in claim 1 wherein the sensing means comprises a plurality of photoelectric sensors, each sensor being affixed to the fingerprint differentiation means in a position to provide for the reception of one or more unique sub-beams.

10. Apparatus as recited in claim 1 further comprising computing means for sequentially emitting sub-beams from the illuminating means so that the reflected sub-beams are received sequentially in a known, selected order by the sensing means.

11. Apparatus as recited in claim 10 further comprising computing means for controlling the sequential emission of sub-beams from the illuminating means and for generating a binary signal for each reflected sub-beam received by the sensing means based upon the intensity of the received sub-beam, sub-beams received for fingerprint valley points being of a higher intensity than sub-beams received for fingerprint ridge points.

12. Apparatus as recited in claim 1 further comprising computing means for controlling the emission of sub-beams from the illuminating means and for generating a binary signal for each reflected sub-beam received by the sensing means based upon the intensity of the received sub-beam, sub-beams received for fingerprint valley points being of a higher intensity than sub-beams received for fingerprint ridge points.

13. Apparatus as recited in claim 1 further comprising digitizing means for generating a binary signal for each sub-beam received by the sensing means, the binary signal being dependent on the intensity of the sub-beam received, sub-beams received for fingerprint valley points being of a higher intensity than sub-beams received for fingerprint ridge points.

14. Apparatus as recited in claim 1 further comprising filter means for preventing radiation of frequencies other than the frequency of radiation emitted by the illuminating means from actuating the sensing means.

15. Apparatus as recited in claim 14 wherein the filter means comprises a narrow band-pass filter.

16. Apparatus as recited in claim 14 wherein the filter means comprises a tuner for the sensing means.

17. Apparatus for sensing fingerprints comprising:
   a) prism having a prism top surface on which one or more fingers of a subject can be pressed for fingerprint sensing, a prism bottom surface and a prism end surface;
   b) illuminating means affixed to the prism bottom surface for internally illuminating points of illumination on the prism top surface with a plurality of sub-beams of illuminating radiation, the angle of incidence of the sub-beams to the prism top surface being selected to provide for reflection to the prism end surface from points of illumination corresponding to fingerprint valley points of the fingers of the subject pressed on the prism top surface and for transmission of sub-beams through the prism top surface at fingerprint ridge points which are in contact with the prism top surface;
   c) sensing means affixed to the prism end surface for sensing illuminating radiation of sub-beams reflected from the prism top surface and generating an electric signal for each sub-beam received.

18. Apparatus as recited in claim 17 wherein the prism is wedge-shaped.

19. Apparatus as recited in claim 17 wherein the illuminating means comprises a surface emitting laser.

20. Apparatus as recited in claim 17 wherein the illuminating means comprises a radiation source and a pixilated LCD.

21. Apparatus as recited in claim 20 wherein the illuminating means further comprises a focusing means for focusing the sub-beams on points of illumination on the prism top surface.

22. Apparatus as recited in claim 21 wherein the focusing means comprises a lens wafer.

23. Apparatus as recited in claim 15 wherein the sensing means comprises a photoelectric sensor.

24. Apparatus as recited in claim 15 wherein the sensing means comprises a plurality of photoelectric sensors, each sensor being affixed to the prism end surface in a position to provide for the reception of a unique sub-beam and wherein each sub-beam is reflected to a unique sensor.

25. Apparatus as recited in claim 15 further comprising computing means for sequentially emitting sub-beams from the illuminating means so that the reflected sub-beams are received sequentially in a known, selected order by the sensing means.

26. Apparatus as recited in claim 25 further comprising computing means for controlling the sequential emission of sub-beams from the illuminating means and for generating a binary signal for each reflected sub-beam received by the sensing means based upon the intensity of the received sub-beam, sub-beams received for fingerprint valley points being of a higher intensity than sub-beams received for fingerprint ridge points.

27. Apparatus as recited in claim 15 further comprising computing means for controlling the emission of sub-beams from the illuminating means and for generating a binary signal for each reflected sub-beam received by the sensing means based upon the intensity of the received sub-beam, sub-beams received for fingerprint valley points being of a higher intensity than sub-beams received for fingerprint ridge points.

28. Apparatus as recited in claim 15 further comprising digitizing means for generating a binary signal for each sub-beam received by the sensing means, the binary signal being dependent on the intensity of the sub-beam received, sub-beams received for fingerprint valley points being of a higher intensity than sub-beams received for fingerprint ridge points.

29. Apparatus as recited in claim 15 further comprising filter means for preventing radiation of frequencies other than the frequency of radiation emitted by the illuminating means from actuating the sensing means.

30. Apparatus as recited in claim 29 wherein the filter means comprises a narrow band-pass filter.

31. Apparatus as recited in claim 29 wherein the filter means comprises a tuner for the sensing means.

32. Apparatus for sensing fingerprints comprising:
   a) prism having a prism top surface on which one or more fingers of a subject can be pressed for fingerprint sensing, a prism bottom surface and a prism end surface;
   b) surface-emitting laser affixed to the prism bottom surface; and
   c) photoelectric sensor affixed to the prism end surface.

33. Apparatus as recited in claim 32 wherein the prism is wedge-shaped.

34. Apparatus as recited in claim 32 wherein the photoelectric sensor comprises a plurality of sensors, each sensor being positioned to provide for the reception of a unique sub-beam and wherein each sub-beam is reflected to a unique sensor.

35. Apparatus as recited in claim 32 further comprising computing means for sequentially emitting sub-beams from the surface emitting laser so that the reflected sub-beams are received by the photoelectric sensor sequentially in a known, selected order by the photoelectric sensor.

36. Apparatus as recited in claim 35 further comprising computing means for controlling the sequential emission of sub-beams from the surface emitting laser and for generating a binary signal for each reflected sub-beam received by the photoelectric sensor and a different binary signal for sub-beams not reflected and received.

37. Apparatus as recited in claim 32 further comprising computing means for controlling the emission of sub-beams from the surface emitting laser, for generating a binary signal for each reflected sub-beam received by the photoelectric sensor and a different binary signal for sub-beams not reflected and received.

38. Apparatus as recited in claim 32 further comprising digitizing means for generating a binary signal for each sub-beam, the binary signal being dependent on whether the sub-beam is reflected and received at the photoelectric sensor or not reflected and thus not received.

39. Apparatus as recited in claim 32 further comprising filter means for preventing radiation of frequencies other than the frequency of radiation emitted by the surface emitting laser from actuating the photoelectric sensor.

40. Apparatus as recited in claim 32 wherein the filter means comprises a narrow band-pass filter.

41. Apparatus as recited in claim 32 wherein the filter means comprises a tuner for the photoelectric sensor.

42. Apparatus for sensing fingerprints comprising:
   a) prism having a prism top surface on which one or more fingers of a subject can be pressed for fingerprint sensing, a prism bottom surface and a prism end surface;
   b) radiation source and pixilated LCD affixed to the prism bottom surface; and
   c) photoelectric sensor affixed to the prism end surface.

43. Apparatus as recited in claim 42 wherein the prism is wedge-shaped.

44. Apparatus as recited in claim 42 further comprising a focusing means for focusing the sub-beams on points of illumination on the prism top surface.

45. Apparatus as recited in claim 44 wherein the focusing means comprises a lens wafer.

46. Apparatus as recited in claim 42 wherein the photoelectric sensor comprises a plurality of sensors, each sensor being positioned to provide for the reception of a unique sub-beam and wherein each sub-beam is reflected to a unique sensor.

47. Apparatus as recited in claim 42 further comprising computing means for sequentially emitting sub-beams from the LCD so that the reflected sub-beams are received by the photoelectric sensor sequentially in a known, selected order by the photoelectric sensor.

48. Apparatus as recited in claim 47 further comprising computing means for controlling the sequential emission of sub-beams from the LCD and for generating a binary signal for each reflected sub-beam received by the photoelectric sensor based upon the intensity of the received sub-beam, sub-beams received for fingerprint valley points being of a higher intensity than sub-beams received for fingerprint ridge points.

49. Apparatus as recited in claim 42 further comprising computing means for controlling the emission of sub-beams from the LCD and for generating a binary signal for each reflected sub-beam received by the photoelectric sensor based upon the intensity of the received sub-beam, sub-beams received for fingerprint valley points being of a higher intensity than sub-beams received for fingerprint ridge points.

50. Apparatus as recited in claim 42 further comprising digitizing means for generating a binary signal for each sub-beam received by the sensing means, the binary signal being dependent on the intensity of the sub-beam received, sub-beams received for fingerprint valley points being of a higher intensity than sub-beams received for fingerprint ridge points.

51. Apparatus as recited in claim 42 further comprising filter means for preventing radiation of frequencies other than the frequency of radiation emitted by the LCD from actuating the photoelectric sensor.

52. Apparatus as recited in claim 51 wherein the filter means comprises a narrow band-pass filter.

53. Apparatus as recited in claim 51 wherein the filter means comprises a tuner for the photoelectric sensor.

54. Apparatus for digitizing fingerprints comprising:
   a) prism having a top contact surface sized for pressing of one or more fingers of a subject for fingerprint sensing and a prism bottom surface for admission of illuminating radiation;
   b) illuminating means for internally illuminating the contact surface with a sequence of sub-beams;
   c) sensing means for detecting sub-beam radiation internally reflected from the contact surface at points of illumination corresponding to fingerprint valleys of the subject fingers and detecting the non-reflection of sub-beam radiation from the contact surface at points of contact between fingerprint ridges and the contact surface; and
   d) digitizing means for digitizing the fingerprints of the subject fingers based upon the sub-beam radiation detected and signals generated by the sensing means.

55. Apparatus as recited in claim 54 wherein the illuminating means is a surface emitting laser.

56. Apparatus as recited in claim 54 wherein the illuminating means is a radiation source and a pixilated LCD.

57. Apparatus as recited in claim 56 wherein the illuminating means further comprises a focusing means for focusing the sub-beams on points of illumination on the contact surface.

58. Apparatus as recited in claim 57 wherein the focusing means comprises a lens wafer.

59. Apparatus as recited in claim 54 wherein the prism is wedge-shaped.

60. Apparatus as recited in claim 54 wherein the sensing means comprises a photoelectric sensor.

61. Apparatus as recited in claim 54 wherein the sensing means comprises a plurality of photoelectric sensors, each sensor being affixed to the prism end surface in a position to provide for the reception of a unique sub-beam and wherein each sub-beam is reflected to a unique sensor.

62. Apparatus as recited in claim 54 further comprising computing means for sequentially emitting sub-beams from the illuminating means so that the reflected sub-beams are received sequentially in a known, selected order by the sensing means.

63. Apparatus as recited in claim 62 further comprising computing means for controlling the sequential emission of sub-beams from the illuminating means and for generating a binary signal for each reflected sub-beam received by the sensing means based upon the intensity of the received sub-beam, sub-beams received for fingerprint valley points being of a higher intensity than sub-beams received for fingerprint ridge points.

64. Apparatus as recited in claim 54 further comprising computing means for controlling the emission of sub-beams from the illuminating means and for generating a binary signal for each reflected sub-beam received by the sensing means based upon the intensity of the received sub-beam, sub-beams received for fingerprint valley points being of a higher intensity than sub-beams received for fingerprint ridge points.

65. Apparatus as recited in claim 54 wherein the digitizing means provides for generating a binary signal for each sub-beam received by the sensing means, the binary signal being dependent on the intensity of the sub-beam received and sub-beams received for fingerprint valley points being of a higher intensity than sub-beams received for fingerprint ridge points.

66. Apparatus as recited in claim 54 further comprising filter means for preventing radiation of frequencies other than the frequency of radiation emitted by the illuminating means from actuating the sensing means.

67. Apparatus as recited in claim 66 wherein the filter means comprises a narrow band-pass filter.

68. Apparatus as recited in claim 66 wherein the filter means comprises a tuner for the sensing means.

69. Method for sensing fingerprints comprising:
   a) step of pressing one or more fingers of a subject on a transparent contact surface,
   b) step of internally illuminating the contact surface at points of illumination with a plurality of sub-beams of illuminating radiation, the angle of incidence of the sub-beams to the contact surface being selected to provide for reflection of the sub-beams from points of illumination corresponding to fingerprint valley points and transmission of sub-beams through the contact surface at fingerprint ridge points;
   c) step of sensing sub-beams reflected from the contact surface and generating an electric signal for each sub-beam received.

70. Method as recited in claim 69 wherein the transparent contact surface comprises a contact surface on a prism.

71. Method as recited in claim 69 wherein the step of illuminating the contact surface is accomplished by a surface-emitting laser.

72. Method as recited in claim 69 wherein the step of illuminating the contact surface is accomplished by a radiation source and a pixilated LCD.

73. Method as recited in claim 72 further comprising the step of focusing each sub-beam on a point of illumination.

74. Method as recited in claim 73 wherein focusing each sub-beam on a point of illumination is accomplished by a lens wafer.

75. Method as recited in claim 69 wherein sensing sub-beams is accomplished by a photoelectric sensor.

76. Method as recited in claim 69 wherein sensing sub-beams is accomplished by a plurality of photoelectric sensors, each of which is affixed in a position to provide for the reception of a unique sub-beam and wherein each sub-beam is reflected to a unique sensor.

77. Method as recited in claim 69 further comprising a step of sequentially emitting sub-beams so that the reflected sub-beams are sensed sequentially in a known, selected order.

78. Method as recited in claim 69 further comprising a step of controlling the sequence of emission of sub-beams and generating a binary signal for each reflected sub-beam received.

79. Method as recited in claim 69 further comprising a step of controlling the emission of sub-beams and generating a binary signal for each reflected sub-beam received based upon the intensity of the received sub-beam, sub-beams received for fingerprint valley points being of a higher intensity than sub-beams received for fingerprint ridge points.

80. Method as recited in claim 69 further comprising a step of generating a binary signal for each sub-beam, the binary signal being dependent on the intensity of the sub-beam received and sub-beams received for fingerprint valley points being of a higher intensity than sub-beams received for fingerprint ridge points.

81. Method as recited in claim 69 wherein a plurality of photoelectric sensors, each sensor being affixed to the prism end surface in a position provides for the reception of a unique sub-beam and wherein each sub-beam is reflected to a unique sensor.

82. Method as recited in claim 69 further comprising a step of excluding radiation of frequencies other than the frequency of illuminating radiation prior to the step of sensing the sub-beams reflected from the contact surface.

83. Method as recited in claim 69 further comprising a step of filtering out frequencies other than the frequency of illuminating radiation prior to the step of sensing.

84. Method as recited in claim 69 wherein the step of sensing further comprises tuning to the frequency of the illuminating radiation.

* * * * *